United States Patent [19]

Yamamoto

[11] Patent Number: 5,075,350

[45] Date of Patent: Dec. 24, 1991

[54] PERFUME COMPOSITIONS PRODUCED BY SOL-GEL METHODS

[76] Inventor: Tohru Yamamoto, c/o Nakato Laboratory, Inc., 6, Ohshinohara, Yasu-cho, Yasu-gun, Japan

[21] Appl. No.: 617,961

[22] Filed: Nov. 26, 1990

Related U.S. Application Data

[63] Continuation of Ser. No. 397,406, Aug. 23, 1989, abandoned.

[30] Foreign Application Priority Data

| Feb. 26, 1987 | [JP] | Japan | 62-043718 |
| Feb. 27, 1987 | [JP] | Japan | 62-045462 |
| Apr. 2, 1987 | [JP] | Japan | 62-082279 |

[51] Int. Cl.$^5$ .............................................. B01D 13/02
[52] U.S. Cl. ........................................ 523/102; 512/4; 524/700; 524/800; 524/837; 427/213.32; 427/213.34; 428/402.21; 428/402.24; 264/4.3; 264/4.7
[58] Field of Search ................ 523/102; 524/700, 800, 524/837; 512/4; 427/213.32, 213.34; 428/402.21, 402.24; 264/4.3, 4.7

[56] References Cited

U.S. PATENT DOCUMENTS

| 3,257,330 | 6/1966 | Burzynski et al. |  |
| 3,551,346 | 12/1970 | Breen et al. |  |
| 3,639,256 | 2/1972 | Horger | 428/402.24 |
| 3,657,143 | 4/1972 | Crainich, Jr. | 428/402.24 |
| 3,730,905 | 5/1973 | Koerner et al. | 428/402.24 |
| 3,791,987 | 2/1974 | Fanger | 428/402.24 |
| 3,870,542 | 3/1975 | Ida et al. |  |
| 4,136,250 | 1/1979 | Mueller et al. |  |
| 4,145,184 | 3/1979 | Brain et al. |  |
| 4,169,069 | 9/1979 | Unger et al. | 428/402.24 |
| 4,370,160 | 1/1983 | Ziemelis |  |
| 4,374,236 | 2/1983 | Znaiden |  |
| 4,382,813 | 5/1983 | Shasha | 427/213.32 |
| 4,411,933 | 10/1983 | Samejima et al. | 428/402.24 |
| 4,500,725 | 2/1985 | Yemoto et al. |  |
| 4,524,018 | 6/1985 | Yemoto et al. |  |
| 4,788,164 | 11/1988 | Che et al. | 428/905 |
| 4,876,039 | 10/1989 | Lo et al. | 512/4 |
| 4,880,851 | 11/1989 | Yamamoto | 512/4 |
| 4,908,233 | 3/1990 | Takazawa et al. | 512/4 |

FOREIGN PATENT DOCUMENTS

| 369168 | 6/1958 | Japan . |
| 54-6251 | 3/1979 | Japan . |
| 58-022063 | 2/1983 | Japan . |

*Primary Examiner*—Melvyn I. Marquis
*Attorney, Agent, or Firm*—Morrison & Foerster

[57] ABSTRACT

Compositions having perfume substance encapsulated or clathrated within are prepared by acid hydrolysis of an aqueous mixture of perfume substance and an alkoxide selected from metal alkoxides, phosphorus alkoxides, and tetraethoxysilane, followed by base catalyzed polycondensation using as a base catalyst N,N-dimenthylbenzylamine, tributylamine, tri-N-propylamine, tri-pentylamine, tripropargylamine, N,N,N-trimethylethylenediamine, or tri-N-hexylamine.

3 Claims, No Drawings

PERFUME COMPOSITIONS PRODUCED BY SOL-GEL METHODS

This application is a continuation of application Ser. No. 07/397,406, filed Aug. 23, 1989, now abandoned which is a division of copending U.S. patent application Ser. No. 160,802, filed Feb. 26, 1988, now U.S. Pat. No. 4,880,851.

BACKGROUND OF THE INVENTION

1. Field of the Invention

This invention relates to an aromatic composition and to a method for its manufacture; in particular, it relates to an aromatic composition that contains aromatic molecules that are encapsulated and/or clathrated, giving continuous aromaticity, and to a method for its manufacture.

2. Description of the Prior Art

In recent years, perfumes (aromatic substances) have been mixed with paints or printing ink so as to lend aromaticity to the coatings of said paints and printing inks. Usually, paints, printing inks, and the like are obtained by dissolving a resin component such as oil, natural resins, synthetic resins, etc., into a solvent, followed by the addition of pigments and dispersants to the solution. For example, to these paints and printing inks, perfumes are added to produce perfumed paint or ink. After the paint (or ink) is coated, the resulting coated layer is heated or dried naturally in the air so that the solvent volatilizes, resulting in the adherence of the resin component that contains perfume. In the method mentioned above, since the perfume is simply mixed with the paint or printing ink, transitory aromaticity can be obtained, but the perfume volatilizes together with the solvent, and long-term aromaticity cannot be maintained. In particular, if the coated layer is heated, the aromaticity is readily lost.

To solve this problem, the microencapsulation of perfumes has been tried. For example, by the coacervation method, molecules of a perfume are covered with a film of gelatin, polyvinyl alcohol (PVA), or the like, resulting in microencapsulated perfume particles with the diameter of 10-100 $\mu$m. Such microencapsulated perfumes are already commercially available. However, the perfume inside the microcapsule is sealed tight with the film of gelatin or PVA, and thus the scent is not released in the condition in which the microcapsules are manufactured. If the film of the capsule is physically destroyed, the scent is released for the first time. When the capsule is broken open, the perfume is released once, and the released perfume volatilizes in a short time. That is, after microcapsules are broken open, the aroma is not maintained for a long time.

SUMMARY OF THE INVENTION

The aromatic composition and the method for producing the same, which are provided by this invention, overcome the problems mentioned above of the conventional compositions and methods.

The aromatic composition of this invention comprises aromatic substances that are encapsulated and/or clathrated in a matrix of inorganic polymer produced from metal alkoxides.

Another aromatic composition of this invention comprises aromatic substances that are encapsulated and/or clathrated in a matrix of conjugated polymer produced from metal alkoxides and silane coupling agents.

Still another aromatic composition of this invention comprises aromatic substances that are encapsulated and/or clathrated in a matrix of conjugated polymer produced from metal alkoxides, organic monomers, and silane coupling agents.

The present invention provides a method for the production of an aromatic composition comprising aromatic substances that are encapsulated and/or clathrated in a matrix of inorganic polymers, which method comprises the steps of: adding an acid catalyst for sol-gel methods to a solution-containing water or a dispersion containing water of metal alkoxides and aromatic substances so as to cause the hydrolysis of said metal alkoxides; and adding a base catalyst for sol-gel methods to the reaction mixture so as to cause the polycondensation of the hydrolysate to form an inorganic polymer, said aromatic substances being encapsulated and/or clathrated in the matrix of said inorganic polymer thereby.

The present invention also provides a method for the production of an aromatic composition comprising aromatic substances that are encapsulated and/or clathrated in a matrix of conjugated polymers, which method comprises the steps of: adding an acid catalyst for sol-gel methods to a solution-containing water or a dispersion containing water of metal alkoxides, silane coupling agents, and aromatic substances so as to cause the hydrolysis of said metal alkoxides and said silane coupling agents; adding a base catalyst for sol-gel methods to the reaction mixture so as to cause the polycondensation of the hydrolysate to form a conjugate polymer, said aromatic substances being encapsulated and/or clathrated in the matrix of said conjugate polymer thereby.

The present invention also provides a method for the production of an aromatic composition comprising aromatic substances that are encapsulated and/or clathrated in a matrix of conjugated polymers, which method comprises the steps of: adding an acid catalyst for sol-gel methods to a solution-containing water or a dispersion containing water of metal alkoxides, silane coupling agents, and aromatic substances so as to cause the hydrolysis of said metal alkoxides and said silane coupling agents; adding organic monomers to the reaction mixture; adding a base catalyst for sol-gel methods to said reaction mixture, and immediately thereafter irradiation the reaction mixture with at least one of these two, ultraviolet light and an electron beam, so that the polycondensation of the hydrolysate occurs with the polymerization of said organic monomers and the hydrolysate of said silane coupling agents to form a conjugated polymer, said aromatic substances being encapsulated and/or clathrated in the matrix of said conjugated polymer thereby.

Thus, the invention described herein makes possible the objectives of (1) providing an aromatic composition in which the aromatic substances are encapsulated and/or clathrated in a matrix of inorganic of conjugated polymer, perfume molecules being released gradually over a long period of time; (2) providing an aromatic composition the aromaticity of which can be released slowly, which composition can be used in the production of, for example, furniture, clothing, cosmetics, building materials, and magnetic cards such as prepaid cards for use in telephoning by being mixed with printing ink, paint, printing materials for clothing, or the like; (3) providing a slow-release composition that has deodorant or insecticidal effects over a long period, which composition is produced by the encapsulation and/or clathration of deodorants, insecticides, or the like in the polymer mentioned above; and (4) providing a method for the production of superior aromatic compositions and slow-release compositions, both of which are mentioned above.

DESCRIPTION OF THE PREFERRED EMBODIMENTS

On the basis of the inventor's knowledge that if it is possible to encapsulate or clathrate perfume molecules inside a porous polymer matrix, an aromatic composition with excellent slow release can be obtained, the inventor completed this invention with regard to an aromatic composition with the use of polymers and a method for producing the same.

The perfume used for the composition of this invention can be natural perfumes of animal origin or plant orgin, or synthetic perfumes. The perfume is used in the proportion of 1–300 parts by weight, and preferably 50–200 parts by weight, for every 100 parts by weight of the metal alkoxides mentioned below. If less than 1 part by weight is used, an aromatic composition of the desired aromaticity cannot be obtained. If more than 300 parts by weight is used, it is difficult to encapsulate the perfume in microcapsules or in polymer matrix.

The metal alkoxides used in the composition of this invention can be obtained by adding methanol, ethanol, isopropanol, and other well-known alcohols to metal oxides such as alumina, silica, titanium(IV) oxide, and zirconium(IV) oxide. For example, $Si(OC_2H_5)_4$, $Al(O-iso-C_3H_7)_3$, $Ti(O-iso-C_3H_7)_4$, $Zr(O-t-C_4H_9)_4$, $Zr(O-n-C_4H_9)_4$, $Ca(OC_2H_5)_2$, $Fe(OC_2H_5)_3$, $V(O-iso-C_3H_7)_4$, $Sn(O-t-C_4H_9)_4$, $Li(OC_2H_5)$, $Be(OC_2H_5)_3$, $V(O-iso-C_3H_7)_4$, $P(OC_2H_5)_3$, and $P(OCH_3)_3$ can be used.

The silane coupling agent used for the composition of this invention can be any of the well-known silane coupling agents, such as ($\gamma$-glycidoxypropyl)trimethoxysilane, ($\gamma$-glycidoxypropyl)methyldiethoxysilane, $\beta$-(3,4-epoxycyclohexyl)ethyltrimethoxysilane, vinyltrimethoxysilane, vinyltrichlorosilane, vinyltris($\beta$-methoxyethoxy)silane, vinyltriacetoxysilane, ($\gamma$-methacryloxypropyl)trimethoxysilane, N-$\beta$-(N-vinylbenzylaminoethyl)-$\gamma$-aminopropyltrimethoxysilane hydrochloride, $\gamma$-aminopropyltriethoxysilane, N-phenyl-$\gamma$-aminopropyltrimethoxysilane, $\gamma$-(2-aminoethyl)aminopropyltrimethoxysilane, $\gamma$-(2-aminoethyl)aminopropylmethyldimethoxysilane, $\gamma$-mercaptopropyltrimethoxysilane, mercaptopropylmethyldimethoxysilane, methyltrimethoxysilane, methyltriethoxysilane, hexamethyldisilazane, $\gamma$-anilinopropyltrimethoxysilane, $\gamma$-chloropropyltrimethoxysilane, $\gamma$-chloropropylmethyldimethoxysilane, methyltrichlorosilane, dimethyldichlorosilane, trimethylchlorosilane, octadecyldimethyl[3-(trimethoxysylil)propyl]ammoniumchloride, a mixture of aminosilanes, etc. For every 100 parts by weight of the metal alkoxide mentioned above, 300 parts by weight or less of the silane coupling agent can be used, with preferably 1–300 parts by weight, and still more preferable limits of 10–40 parts by weight. If more than 300 parts by weight is used, the polymer obtained is not very different from that obtained with less, and is expensive.

As organic monomers, there are acrylic acid, metharylic acid, dimethylformamide, acrylonitrile, stylene, methyl acrylate, ethyl acrylate, methyl methacrylate, ethyl methacrylate, etc. However, any vinyl-type monomer, and not just those listed here, can be used.

This kind of organic monomer is used within the limits of 200 parts by weight or less for every 100 parts by weight of the metal alkoxide mentioned above, and preferably 10–300 parts by weight, with still more preferable limits of 30–100 parts by weight.

The catalyst for sol-gel method (which is used to catalyze hydrolysis and polycondensation reactions for the metal alkoxides and silane coupling agents mentioned above) includes acids, their anhyrides, and organic bases. These organic bases are tertiary amines that are substantially insoluble in water and soluble in organic solvents.

As the acid used as a catalyst, it is possible to use mineral acid such as hydrochloric acid, sulfuric acid, nitric acid, etc. It is possible to obtain the same effects with the use of the anhydride of mineral acids, for example, with hydrogen chloride gas. Also, organic acids and their anhydrides can be used. For example, tartaric acid, phthalic acid, maleic acid, dodecylsuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride can be used. Per mole of the metal alkoxide, 0.01 mol or more of these acids, and preferably 0.01–0.5 mol, can be used. If the amount of the acid is less than 0.01 mol, the hydrolysis of the metal alkoxides does not proceed substantially.

As such tertiary amines used as a catalyst, N,N-dimethylbenzylamine, tributylamine, tri-n-propylamine, tripentylamine, tripropargylamine, N,N,N-trimethylethylenediamine, tri-n-hexylamine, etc., can be used. The tertiary amine can be used at equimolar amounts or in excess amounts of the acid mentioned above; preferably, it is used in amounts ranging from 0.01 to 0.06 mol per mole of the metal alkoxide. The amount of tertiary amine to be used can be chosen within the limits mentioned above with consideration of its degree of dissociation. If there is too little tertiary amine, than after the hydrolysis of the metal alkoxide, the rate of polycondensation is greatly slowed.

As the solvent that can be used in the method, in addition to the water used in the hydrolysis, it is possible to use an organic solvent. As the organic solvent, solvents that are miscible with water or solvents that can be partly dissolved in water can be used. These include, for example, methanol, ethanol, butanol, n-propanol, isopropanol, pentanol, hexanol, acetone, methyl ethyl ketone, and formamide.

The aromatic composition of this invention is manufactured by the following three main methods. In the first method, a polymer is made by the use of a metal alkoxide, and the perfume is trapped in a matrix of this polymer. In the second method, a polymer is made by the use of a metal alkoxide and a silane coupling agents, and the perfume is trapped in a matrix of this polymer. In the third method, a polymer is made by the use of a metal alkoxide, silane coupling agent, and organic monomer, and the perfume is trapped in a matrix of this polymer.

In the first method, for example, the metal alkoxide mentioned above is dissolved in the organic solvent mentioned above, such as, for example, alcohol. The concentration of the metal alkoxide is not set within any particular limits, but ordinarily, it is 500–600 g/l. Next, water is added to the metal alkoxide solution. The amount of water that is added is at the proportion of 1-30 moles per mole of the metal alkoxide. The water can be mixed beforehand with the alcohol mentioned above. To this solution of metal alkoxide (including water), the perfume mentioned above is added to obtain a solution or dispersion. The perfume can be added, for example, in the form of a solution in organic solvent or aqueous solution. To this, an acid (or its anhydride) catalyst for the sol-gel method mentioned above is added and the mixture is mixed at room temperature. The reaction is carried out at room temperature to prevent the volatilization of the perfume. With this treatment, hydrolysis is virtually complete. Into this reaction mixture, the tertiary amine catalyst (the other of the two forms of the catalyst) is added. When the tertiary amine is added, a polycondensation reaction proceeds and gelatin is completed within a relatively short time. The time taken for gelation or degree of gelation depends on the amount of water used and the amount of catalyst for the sol-gel method that is used. In general, it is possible to control the time of gelation from about 2 seconds to several dozens of minutes.

The gel mentioned above is constituted by an inorganic polymer formed by the hydrolysis and polycondensation of the metal alkoxide mentioned above. Perfume particles (i.e., fine granules of solid or liquid comprising molecules of perfume, and as the case may be, the organic solvent that containes the molecules of perfume) are trapped in a matrix of this polymer. More particularly, it is possible to encapsulate and/or clathrate particles of perfume in the following kind of form. In the reaction mentioned above, the metal alkoxide undergoes hydrolysis and polycondensation, including a cross-linking reaction, resulting in fine particles with a three-dimensional structure. When the particles with a three-dimensional structure is formed, the particles of perfume are trapped into the three-dimensional network constituted by the said structure. As a result, the particles of perfume are encapsulated in particles of polymer. These polymer particles gather in a number of clumps, and they further undergo polycondensation and cross-linking reactions to form a continuous three-dimensional matrix. The perfume particles are taken into the spaces inside, so as to be encapsulated or clathrated. When the solvent including alcohol produced by the polycondensation reaction is removed by volatilization from the three-dimensional matrix, as will be described below, the perfume remains in the porous matrix framework. It is known that the pores of the porous matrix mentioned above have an extremely small diameter (Science, Vol. 79, 192 (1986); Nikkei Science Inc.). For that reason, the perfume volatilizes gradually, which results in the fragrance continuing long-term.

In the second method, a silane coupling agent is used in addition to the metal alkoxide of the first method described above. For example, first, to a solution that contains metal alkoxide in alcohol and water, perfume, silane coupling agent, and a light-sensitizer, if needed, are added. As the light-sensitizer, diacetyl and the like can be used. The light-sensitizer accelerates the photocondensation reaction brought about by the ultraviolet radiation. Moreover, if needed, other monomers and polymers can be added. As such monomers, there are vinyl-type monomers, and as the polymers, there are copolymers and polymers polymerized from vinyl chloride, vinyl acetate, butadiene, etc. These monomers and polymers are added for the purpose of acceleration of the polymerization and copolymerization reactions described below, and for the purpose of the formation of a homogeneous and strong polymer.

To this mixture, as in the first method described above, a catalyst for the sol-gel methods is added, and the mixture is irradiated as needed by ultraviolet light and/or by an electron beam. The wavelength of the ultraviolet light is 250 nm or less. If this wavelength is more than 250 nm, the radical polymerization, cross-linking reaction, and polycondensation reaction mentioned below will probably not proceed sufficiently. The dose of radiation with an electron beam can be within the limits of 0.1-50 megarads. The amount of energy is preferably 150-200 kV. If less than 0.1 megarad is used, the radical polymerization, cross-linking reaction, and polycondensation reaction mentioned below will probably not proceed sufficiently. There is no need for more than 50 megarads. The radiation equipment for the electron beam can be, for example, an area beam electronic radiation device such as the Curetron (Nisshin Denki Co.).

The metal alkoxide and silane coupling agent in the reaction mixture mentioned above are hydrolyzed, followed by the subsequent polycondensation reaction, which proceeds rapidly. Moreover, when the silane coupling agent contains, for example, an epoxy moiety, the acid and base catalyst mentioned above cause cleavage of the epoxy ring, and ring-opening polymerization occurs. When a reaction mixture is irradiated with ultraviolet light and/or an electron beam, radicals arise from vinyl groups, and these radicals cause the cross-linking reaction and radical polymerization (i.e., photopolymerization or electronbeam polymerization) of the organic portion of the silane coupling agent. When ultraviolet light is used for radiation, the radicals arise from the light-sensitizer. In addition to an electron beam and ultraviolet light, other kinds of radiation can be used.

In these ways, the hydrolysis and polycondensation of the metal alkoxide and the inorganic portion of the silane coupling agent are made to proceed rapidly. Radical polymerization (including cross-linking polymerization) of the organic portion of the silane coupling agent can also be made to proceed rapidly. The reactions mentioned above occur between the silane coupling agents, between the metal alkoxides, and/or between the silane coupling agent and the metal alkoxide. The inorganic portion of the silane coupling agent (i.e., the silica portion) is taken into the framework of inorganic polymer molecules produced from the hydrolysate of the metal alkoxide, or forms an inorganic polymer by polycondensation arising among the silane coupling agents. The organic portion of the silane coupling agent that is attached to the silicon atom forms a cross-linked moiety with an organic portion of the other silane coupling agent molecule.

The polymer formed in this way has an inorganic polymer portion formed from the hydrolysis and polycondensation of the metal alkoxide and the silane coupling agent and also an organic polymer portion formed by the polymerization of the polymerizable group (i.e., organic portion) of the silane coupling agent. In other words, the metal alkoxide and the silane coupling agent react to form a polymer in which the metal alkoxide and the silane coupling agent are bound on the molecular level (this can be thought of as a conjugated polymer with an organic portion and an inorganic portion). The reaction system containing the said polymer becomes a gel, as in the first method mentioned above. The conjugated polymer forms a matrix with a three-dimensional structure that is almost the same structure as in the first method, and the perfume particles that are present in the reaction system are encapsulated or clathrated in the polymer matrix almost in the same way as in the first method.

In the third method, in addition to the metal alkoxide and silane coupling agents used in the second method mentioned above, an organic monomer is used. For example, first, to a solution of metal alkoxide in water and alcohol, perfume and silane coupling agent are added. To the mixture, an acid catalyst for solgel methods is added so as to hydrolyze the metal alkoxide, followed by the addition of the organic monomer. When photocondensation is carried out by the use of ultraviolet light, a light-sensitizer such as diacetyl can be added. Furthermore, other monomers and polymers can be added as in the second method, if needed. To this mixture, a base catalyst for sol-gel methods is added, and the mixture is irradiated with ultraviolet light and/or an electron beam. The reaction that is brought about in this way is similar to the reaction in the second method, and polymerization of organic monomers by a radical reaction occurs. This polymerization can occur between molecules of the organic monomer, and also between molecules of the said organic monomer and the organic portion (e.g., the epoxy moiety, vinyl moiety, etc.) of the silane coupling agent. In this way, a conjugated polymer is produced that has more organic portions than those of the polymer of the second method, and that has a complicated cross-linked structure. The perfume particles are encapsulated and/or clathrated in the conjugated polymer matrix as in the first and second methods described above.

In general, as a catalyst for sol-gel methods, mineral acids are widely known, but if such catalysts are used in the third method, compared to the polymerization of organic monomers, the hydrolysis and polycondensation reactions of the metal alkoxides and silane coupling agent become extremely slow. As a result, a homogeneous conjugated polymer is not formed. On the contrary, in this invention, catalysts for sol-gel methods mentioned above that has been developed by the inventors are used, and the reaction is very much accelerated, so that an homogeneous conjugated polymer is formed.

When an electron beam and/or ultraviolet light is used for radical polymerization in the second and third methods described above, the reaction proceeds at low temperatures such as 20°-30° C. so that the perfume will not volatilize and be lost. With the composition obtained by the use of the first and second methods, when the solvent and the alcohol are removed from the reaction system (including the framework of the matrix), a porous polymer matrix including perfume particles can be obtained. For that reason, with this composition as well, the slow release of the perfume is very satisfactory. The conjugated polymer in the composition obtained by these methods includes an organic portion in the molecule, so the rate of film formation, mechanical strength, processability, and adhesion to various kinds of base materials are excellent. For that reason, by application to base materials such as wood, synthetic resin, metals, fabrics, non-woven cloth, etc. with a paint to which this composition is added, various kinds of products with aromaticity having excellent slow release properties and with excellent durability can be obtained.

In general, the reaction mixtures that contain perfume particles that are encapsulated or clathrated by the first, second, and third methods described above are gels. The reaction mixture may be a sol that contains fine polymer particles, and the sol may also be used for various purposes. When the gel is mashed, for example, it can be mixed with printing ink or paint to give ink or paint with aromaticity. Alternatively, the gel can be dried, to give a porous polymer that contains perfume, and this can be mixed with paints and the like. This kind of ink and paint can be applied to fabric goods, building materials, furniture, etc., or these articles can be soaked in it. It is also possible to include this in cosmetics. In place of the perfume, insecticides or deodorants can be encapsulated and/or clathrated to give them long-lasting effects. The various products on which the composition of this invention is used can maintain their aromaticity, insecticidal properties, or deodorant effects long-term.

EXAMPLE 1

| Components | Amounts | (molar ratio) |
|---|---|---|
| Ethyl silicate | 25 g | (1) |
| Water | 8.6 g | (4) |
| Ethanol | 25 ml | |
| Aldehyde-type perfume | 25 g | |
| Hydrochloric acid | 0.129 g[a] | (0.03) |
| N,N-Dimethylbenzylamine | 0.321 g | (0.02) |

NOTE:
[a]Calculated in terms of hydrogen chloride.

After the ethanol, ethyl silicate, and perfume were mixed, water and hydrochloric acid were added, and the mixture was stirred for several seconds. N,N-Dimethylbenzylamine was added, and the mixture was stirred for 50 seconds more to obtain a gel. Next, the resulting gel was mashed and then dispersed evenly in printing ink (which contained 255 g of urethane-acrylate polymer emulsion and 7.2 g of pigment.)

The aromatic ink composition obtained was applied on the surface of cotton cloth, and was found to have uniform aromaticity for 8 months. When printing ink that contained acrylate-polymer emulsion instead of the urethane-acrylate polymer emulsion was used, the same results were obtained.

EXAMPLE 2

| Components | Amounts | (molar ratio) |
|---|---|---|
| Ethyl silicate | 25 g | (1) |
| Water | 8.6 g | (4) |
| Ethanol | 25 ml | |
| (γ-Glycidoxypropypl) trimethoxysilane (Tore silicone SH6040) | 6 g | |
| Aldehyde-type perfume | 25 g | |
| Hydrochloric acid | 0.129 g[a] | (0.03) |
| N,N-Dimethylbenzylamine | 0.162 g | (0.01) |

NOTE:
[a]Calculated in terms of hydrogen chloride.

Ethanol, ethyl silicate, perfume, silane coupling agent (Tore silicone SH 6040), and water were mixed, and then hydrochloric acid and N,N-dimethylbenzylamine was added in this order by the same method as in Example 1. The resulting gel was mashed and then mixed uniformly in an ethanol solution containing 90% of nylon 6/11. This mixture was applied to the surface of a sheet made of polyvinyl chloride so that it would be 20 μm thick after drying. The scent lasted for 2 months.

EXAMPLE 3

| Components | Amounts | (molar ratio) |
|---|---|---|
| Ethyl silicate | 25 g | (1) |
| Water | 4.3 g | (2) |
| Isopropyl alcohol | 20 ml | |
| Acetone | 10 ml | |
| (γ-Glycidoxypropyl) trimethoxysilane (Tore silicone SH6040) | 7 g | |
| Ester-type perfume | 20 ml | |
| Hydrochloric acid | 0.129 g[a] | (0.03) |
| N,N-Dimethylbenzylamine | 0.162 g | (0.01) |

NOTE:
[a]Calculated in terms of hydrogen chloride.

In place of ethanol, isopropyl alcohol was used, and a reaction was carried out as in Example 2. The resulting gel was mashed and then mixed with acetone. Cloth (100% cotton broadcloth) was soaked in this mixture, removed, and then dried. The amount of mixture that remained on the cloth per unit area after drying was 13.8 g/m$^2$. This aromatic cloth remained scented for 6 months.

EXAMPLE 4

| Components | Amounts | (molar ratio) |
|---|---|---|
| Ethyl silicate | 25 g | (1) |
| Water | 4.3 g | (2) |
| Isopropyl alcohol | 25 ml | |
| Acetone | 12 ml | |
| (γ-Glycidoxypropyl) trimethoxysilane (Tore silicone SH6040) | 6 g | |
| Acrylonitrile | 18.9 ml | |
| Ester-type perfume | 10 ml | |
| Hydrochloric acid | 0.129 g[a] | (0.03) |
| N,N-Dimethylbenzylamine | 0.324 g | (0.02) |

NOTE:
[a]Calculated in terms of hydrogen chloride.

Isopropyl alcohol, ethyl silicate, perfume, silane coupling agent, acrylonitrile monomer and water were mixed, and to this, hydrochloric acid and N,N-dimethyl-benzylamine was added in that order by the same method used in Example 1. The gel that was produced was mashed and diluted with acetone. The mixture was coated on the surface of glass plate so that it would be 10 μm thick after drying. The scent lasted for 2 months.

EXAMPLE 5

| Components | Amounts | (molar ratio) |
|---|---|---|
| Ethyl silicate | 25 g | (1) |
| Water | 8.6 g | (4) |
| Ethanol | 25 ml | |
| Deodorant (Fresh-Shuraimatsu; Shiraimatsu Inc.) | 50 g | |
| Hydrochloric acid | 0.129 g[a] | (0.03) |
| N,N-Dimethylbenzylamine | 0.324 g | (0.02) |

NOTE:
[a]Calculated in terms of hydrogen chloride.

Ethyl silicate, ethanol, deodorant, and water were mixed, and then hydrochloric acid and N,N-dimethyl-benzylamine were added in this order by the same method as in Example 1. The resulting gel was mashed and then applied on the internal surface of a plastic garbage container for use in kitchens. The deodorant effects were retained for 2 months.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A perfume composition comprising perfume substances encapsulated or clathrated in a matrix of polymer produced from an alkoxide selected from the group consisting of metal alkoxides, silicon alkoxides, and phosphorous alkoxides, which is obtained from the method comprising the steps of:
    (a) adding an acid catalyst for sol-gel methods to an aqueous mixture of:
        (i) alkoxides from the group consisting of metal alkoxides, silicon alkoxides, and phosphorous alkoxides; and
        (ii) perfume substances; so as to cause the hydrolysis of said alkoxides; and
    (b) adding a base catalyst for sol-gel methods to the reaction mixture so as to cause the polycondensation of the hydrolysate to form a polymer, thereby encapsulating the perfume substances or clathrating the perfume substances in the matrix of the polymer;
wherein the base catalyst is selected from the group consisting of N,N-dimethylbenzylamine, tributylamine, tri-N-propylamine, tripentylamine, tripropargylamine, N,N,N-trimethylethylenediamine, and tri-N-hexylamine.

2. A perfume composition according to claim 1, wherein said alkoxide is selected from the group consisting of $Si(OC_2H_5)_4$, $Al(O\text{-iso-}C_3H_7)_3$, $Ti(O\text{-iso-}C_3H_7)_3$, $Zr(O\text{-t-}C_4H_9)_4$, $Zr(O\text{-N-}C_4H_9)_4$, $Ca(OC_2H_5)_2$, $Fe(OC_2H_5)_3$, $V(O\text{-iso-}C_3H_7)_3$, $Sn(O\text{-t-}C_4H_9)_4$, $Li(OC_2H_5)_2$, $Be(OC_2H_5)_3$, $P(OC_2H_5)_2$, and $P(OCH_3)_3$.

3. A perfume composition according to claim 1, wherein said perfume comprises at least one major ingredient selected from the group consisting of natural perfumes of animal or plant origin and synthetic perfumes.

* * * * *